(12) United States Patent
Daskeviciene et al.

(10) Patent No.: US 7,534,541 B2
(45) Date of Patent: May 19, 2009

(54) HETEROCYCLE-HYDRAZONE BASED CHARGE TRANSPORT MATERIALS

(75) Inventors: Maryte Daskeviciene, Jonava (LT);
Vytautas Getautis, Kaunas (LT);
Tadeus Lozovski, Rudamina (LT);
Edmundas Montrimas, Vilnius (LT)

(73) Assignee: Samsung Electronics Co., Ltd., Suwon (KR)

( * ) Notice: Subject to any disclaimer, the term of this patent is extended or adjusted under 35 U.S.C. 154(b) by 483 days.

(21) Appl. No.: 11/044,966

(22) Filed: Jan. 27, 2005

(65) Prior Publication Data

US 2006/0166118 A1      Jul. 27, 2006

(51) Int. Cl.
*G03G 5/06* (2006.01)
(52) U.S. Cl. .................. 430/75; 430/58.15; 430/58.4; 430/58.45; 430/76; 430/77; 549/59; 549/76; 549/491; 548/561
(58) Field of Classification Search ............ 430/75, 430/58.15, 58.4, 58.45, 77, 76, 58.5; 549/59, 549/76, 491; 548/561
See application file for complete search history.

(56) References Cited

U.S. PATENT DOCUMENTS

| | | | | |
|---|---|---|---|---|
| 4,861,691 A | * | 8/1989 | Kuroda et al. ............ | 430/58.15 |
| 4,957,837 A | * | 9/1990 | Kuroda et al. ............ | 430/58.15 |
| 4,985,325 A | * | 1/1991 | Kuroda et al. ............ | 430/58.15 |
| 5,080,991 A | * | 1/1992 | Ono et al. ................ | 430/73 |
| 6,210,847 B1 | * | 4/2001 | Miyauchi et al. .......... | 430/58.4 |
| 7,220,523 B2 | * | 5/2007 | Tokarski et al. ........... | 430/77 |
| 2005/0277039 A1 | * | 12/2005 | Lygaitis et al. ............ | 430/77 |

FOREIGN PATENT DOCUMENTS

| | | |
|---|---|---|
| JP | 56-081552 | 7/1981 |
| JP | 57-190951 | 11/1982 |
| JP | 63-061259 | 3/1988 |

* cited by examiner

*Primary Examiner*—Mark F Huff
*Assistant Examiner*—Rachel L. Burney
(74) *Attorney, Agent, or Firm*—DLA Piper LLP US

(57) ABSTRACT

Improved organophotoreceptor comprises an electrically conductive substrate and a photoconductive element on the electrically conductive substrate, the photoconductive element comprising:

(a) a charge transport material having the formula:

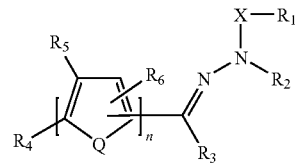

where n is an integer between 1 and 10, inclusive;
$R_1$ comprises a functional group selected from the group consisting of a reactive ring group, an ethylenically unsaturated group, a reactive polar group, a hydrazone group, and an azine group;
$R_2$, $R_3$, $R_4$, $R_5$, and $R_6$ comprise, each independently, H, an alkyl group, an alkenyl group, an alkynyl group, an aromatic group, a heterocyclic group, or a part of a ring group;
X is a bond or a linking group; and
Q is O, S, or NR where R is H, an alkyl group, an acyl group, an alkenyl group, an alkynyl group, a heterocyclic group, or an aromatic group; and
(b) a charge generating compound.

27 Claims, No Drawings

HETEROCYCLE-HYDRAZONE BASED CHARGE TRANSPORT MATERIALS

FIELD OF THE INVENTION

This invention relates to organophotoreceptors suitable for use in electrophotography and, more specifically, to organophotoreceptors including a charge transport material having a heterocycle hydrazone comprising at least a functional group bonded through a bond or a linking group to a hydrazone nitrogen where the functional group is selected from the group consisting of a reactive ring group, an ethylenically unsaturated group, a reactive polar group, an azine group, and a hydrazone group.

BACKGROUND OF THE INVENTION

In electrophotography, an organophotoreceptor in the form of a plate, disk, sheet, belt, drum, or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

(a) a charge transport material having the formula:

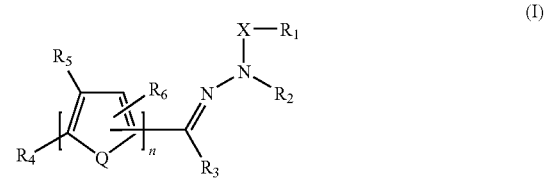

where n is an integer between 1 and 10, inclusive;

$R_1$ comprises a functional group selected from the group consisting of a reactive ring group, such as an epoxy group, a thiiranyl group, an aziridinyl group, and an oxetanyl group, an ethylenically unsaturated group, such as a vinyl ether group, an alkenyl group, an acryloyl group, a methacryloyl group, an acrylamido group, and a methacrylamido group, a reactive polar group, such as a hydroxyl group, a thiol group, a carboxyl group, and an amino group, a hydrazone group, and an azine group;

$R_2$, $R_3$, $R_4$, $R_5$, and $R_6$ comprise, each independently, H, an alkyl group, an alkenyl group, an alkynyl group, an aromatic group, a heterocyclic group, or a part of a ring group, such as cycloalkyl groups, heterocyclic groups, and a benzo group;

X is a bond or a linking group, such as a $—(CH_2)_m—$ group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen; and Q is O, S, or NR where R is H, an alkyl group, an acyl group, an alkenyl group, an alkynyl group, a heterocyclic group, or an aromatic group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser, such as a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having Formula (I) above.

The invention provides suitable charge transport materials for organophotoreceptors featuring a combination of good mechanical and electrostatic properties. These photoreceptors can be used successfully with toners, such as liquid toners and dry toners, to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element including a charge generating compound and a charge transport material having a heterocycle hydrazone comprising at least a functional group bonded through a bond or a linking group to a hydrazone nitrogen where the functional group is selected from the group consisting of a reactive ring group, an ethylenically unsaturated group, a reactive polar group, an azine group, and a hydrazone group. The heterocycle may comprise a fused-ring substituent such as a benzo ring. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

Charge transport materials may comprise monomeric molecules (e.g., N-ethyl-carbazolo-3-aldehyde N-methyl-N-phenyl-hydrazone), dimeric molecules (e.g., disclosed in U.S. Pat. Nos. 6,140,004, 6,670,085 and 6,749,978), or polymeric compositions (e.g., poly(vinylcarbazole)). The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, and the charge transport compounds described in U.S. Pat. Nos. 6,670,085, 6,689,523, 6,696,209, 6,749,978, 6,768,010, 6,815,133, 6,835,513, and 6,835,514, and U.S. patent application Ser. Nos. 10/431,135, 10/431, 138, 10/699,364, 10/663,278, 10/699,581, 10/748,496, 10/789,094, 10/644,547, 10/749,174, 10/749,171, 10/749, 418, 10/699,039, 10/695,581, 10/692,389, 10/634,164, 10/749,164, 10/772,068, 10/749,178, 10/758,869, 10/695, 044, 10/772,069, 10/789,184, 10/789,077, 10/775,429, 10/670,483, 10/671,255, 10/663,971, 10/760,039, 10/815, 243, 10/832,596, 10/836,667, 10/814,938, 10/834,656, 10/815,118, 10/857,267, 10/865,662, 10/864,980, 10/865, 427, 10/883,453, 10/929,914, and 10/900,785. All the above patents and patent applications are incorporated herein by reference.

Non-limiting examples of electron transport compounds include, for example, bromoaniline, tetracyanoethylene, tetracyanoquinodimethane, 2,4,7-trinitro-9-fluorenone, 2,4,5, 7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzothiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2, 6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene) malonate, anthraquinodimethane derivatives such as 11,11, 12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl)methylene]anthrone, 1,8-dihydroxy-10-[bis(ethoxycarbonyl)methylene]anthrone, and 1-cyano-10-[bis (ethoxycarbonyl)methylene)anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8- trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinodimethane, 2,4,5,7-tetranitro-9-fluorenone, 2,4,7-trinitro-9-dicyanomethylene fluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232,800, 4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example:

(a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula:

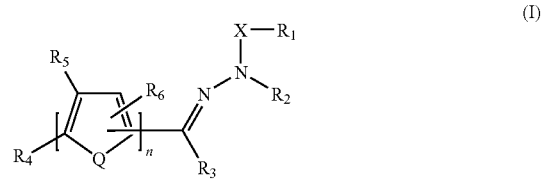

(I)

where n is an integer between 1 and 10, inclusive;

$R_1$ comprises a functional group selected from the group consisting of a reactive ring group, such as an epoxy group, a thiiranyl group, an aziridinyl group, and an oxetanyl group, an ethylenically unsaturated group, such as a vinyl ether group, an alkenyl group, an acryloyl group, a methacryloyl group, an acrylamido group, and a methacrylamido group, a reactive polar group, such as a hydroxyl group, a thiol group, a carboxyl group, and an amino group, a hydrazone group, and an azine group;

$R_2$, $R_3$, $R_4$, $R_5$, and $R_6$ comprise, each independently, H, an alkyl group, an alkenyl group, an alkynyl group, an aromatic group, a heterocyclic group, or a part of a ring group, such as cycloalkyl groups, heterocyclic groups, and a benzo group;

X is a bond or a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a P(=O)$R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen; and Q is O, S, or NR where R is H, an alkyl group, an acyl group, an alkenyl group, an alkynyl group, a heterocyclic group, or an aromatic group.

A heterocyclic group includes any monocyclic or polycyclic (e.g., bicyclic, tricyclic, etc.) ring compound having at least a heteroatom (e.g., O, S, N, P, B, Si, etc.) in the ring. Furthermore, the heterocyclic group may be aromatic or non-aromatic.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furyl, thienyl, pyrrolyl, indolyl, indolizinyl, isoindolyl, pyrazolyl, imidazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4) dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, the linking group may comprise at least one heteroatom such as O, S, Si, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, the linking group may comprise at least one heteroatom such as O, S, Si, and N.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, alkenyl group, alkynyl group, phenyl group, aromatic group, heterocyclic group, hydrazone group, azine group, fluorenyl group, fluorenylidene group, acyl group, amino group, oxiranyl group, oxetanyl group, thiiranyl group, aziridinyl group, acrylate group, methacrylate group, etc.) may have any substituent thereon which is consistent with the bond structure of that group. For example, where the term 'alkyl group' or 'alkenyl group' is used, that term would not only include unsubstituted linear, branched and cyclic alkyl group or alkenyl group, such as methyl, ethyl, ethenyl or vinyl, isopropyl, tert-butyl, cyclohexyl, cyclohexenyl, dodecyl and the like, but also substituents having heteroatom(s), such as 3-ethoxylpropyl, 4-(N,N-diethylamino)butyl, 3-hydroxypentyl, 2-thio]hexyl, 1,2,3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N, N-disubstituted)aminophenyl, 2,4-dihydroxyphenyl, 2,4,6-trithiophenyl, 2,4,6-trimethoxyphenyl and the like would be acceptable within the terminology, while substitution of 1,1, 2,2,3,3-hexamethylphenyl would not be acceptable as that substitution would require the ring bond structure of the phenyl group to be altered to a non-aromatic form. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester [e.g., poly(ethylene terephthalate) or poly(ethylene naphthalate)], polyimide, polysulfone, polypropylene, nylon, polyester, polycarbonate, polyvinyl resin, poly(vinyl fluoride), polystyrene and the like. Specific examples of polymers for supporting substrates included, for example, polyethersulfone (STABAR™ S-100, available from ICI), poly(vinyl fluoride) (TEDLAR®, available from E.I. DuPont de Nemours & Company), polybisphenol-A polycarbonate (MAKROFOL™, available from Mobay Chemical Company) and amorphous poly(ethylene terephthalate) (MELINAR™ available from ICI Americas, Inc.). The electrically conductive materials may be graphite, dispersed carbon black, iodine, conductive polymers such as polypyrroles and CALGON® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers (such as a dye or pigment). Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the LV stabilizers may not be their LV stabilizing abilities, although the LV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as TINUVIN™ 144 and TINUVIN™ 292 (from Ciba Specialty Chemicals, Terrytown, N.Y.), hindered alkoxydialkylamines such as TINUVIN™ 123 (from Ciba Specialty Chemicals), benzotriazoles such as TINUVIN™ 328, TINUVIN™ 900 and TINUVIN™ 928 (from Ciba Specialty Chemicals), benzophenones such as SANDUVOR™ 3041 (from Clariant Corp., Charlotte, N.C.), nickel compounds such as ARBESTAB™ (from Robinson Brothers Ltd, West Midlands, Great Britain), salicylates, cyanocinnamates, benzylidene malonates, benzoates, oxanilides such as SANDUVOR™ VSU (from Clariant Corp., Charlotte, N.C.), triazines such as CYAGARD™ UV-1164 (from Cytec Industries Inc., N.J.), polymeric sterically hindered amines such as LUCHEM™ (from Atochem North America, Buffalo, N.Y.). In some embodiments, the light stabilizer is selected from the group consisting of hindered trialkylamines having the following formula:

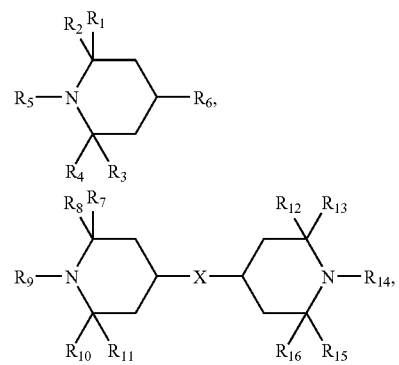

where $R_1, R_2, R_3, R_4, R_6, R_7, R_8, R_{10}, R_{11}, R_{12}, R_{13}, R_{14}, R_{15}$ are, each independently, hydrogen, alkyl group, or ester, or ether group; and $R_5, R_9,$ and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, poly(styrene-co-butadiene), poly(styrene-co-acrylonitrile), modified acrylic polymers, poly(vinyl acetate), styrene-alkyd resins, soya-alkyl resins, poly(vinylchloride), poly(vinylidene chloride), polyacrylonitrile, polycarbonates, poly(acrylic acid), polyacrylates, polymethacrylates, styrene polymers, poly(vinyl butyral), alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether-co-dicyclopentadiene), copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. IUPILON™ A from Mitsubishi Engineering Plastics, or LEXAN™ 145 from General Electric); polycarbonate Z which is derived from cyclohexylidene bisphenol (e.g. IUPILON™ Z from Mitsubishi Engineering Plastics Corp, White Plain, New York); and polycarbonate C which is derived from methyl-bisphenol A (from Mitsubishi Chemical Corporation). Non-limiting examples of suitable polyester binders include ortho-polyethylene terephthalate (e.g. OPET™ TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport material generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport material and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as poly(vinyl alcohol), methyl vinyl ether/maleic anhydride copolymer, casein, poly(vinyl pyrrolidone), poly(acrylic acid), gelatin, starch, polyurethanes, polyimides, polyesters, polyamides, poly(vinyl acetate), poly (vinyl chloride), poly(vinylidene chloride), polycarbonates, poly(vinyl butyral), poly(vinyl acetoacetal), poly(vinyl formal), polyacrylonitrile, poly(methyl methacrylate), polyacrylates, poly(vinyl carbazoles), copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the protective layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, poly(methyl methacrylate), poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

As described herein, an organophotoreceptor comprises a charge transport material having the formula:

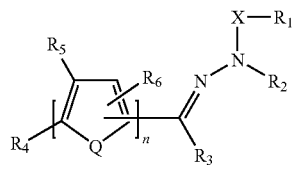

(I)

where n is an integer between 1 and 10, inclusive;

$R_1$ comprises a functional group selected from the group consisting of a reactive ring group, such as an epoxy group, a thiiranyl group, an aziridinyl group, and an oxetanyl group, an ethylenically unsaturated group, such as a vinyl ether group, an alkenyl group, an acryloyl group, a methacryloyl group, an acrylamido group, and a methacrylamido group, a reactive polar group, such as a hydroxyl group, a thiol group, a carboxyl group, and an amino group, a hydrazone group, and an azine group;

$R_2$, $R_3$, $R_4$, $R_5$, and $R_6$ comprise, each independently, H, an alkyl group, an alkenyl group, an alkynyl group, an aromatic group, a heterocyclic group, or a part of a ring group, such as cycloalkyl groups, heterocyclic groups, and a benzo group;

X is a bond or a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a P(=O)$R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen; and Q is O, S, or NR where R is H, an alkyl group, an acyl group, an alkenyl group, an alkynyl group, a heterocyclic group, or an aromatic group.

In some embodiments of interest, the X group is a bond or a —$(CH_2)_m$— group, where m is an integer between 1 and 10, inclusive. In other embodiments of interest, $R_1$ is selected from the group consisting of an epoxy group, a thiiranyl group, an aziridinyl group, an oxetanyl group, a vinyl ether group, an alkenyl group, an acryloyl group, a methacryloyl group, an acrylamido group, and a methacrylamido group. In other embodiments of interest, Q is S and n is an integer between 2 and 5, inclusive. In further embodiments of interest, $R_4$ and $R_5$ of Formula (I) together form a benzo ring and n is 1. In additional embodiments of interest, $R_1$ comprises a heterocycle hydrazone group having the formula:

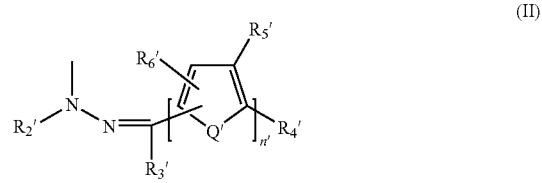

(II)

where n' is an integer between 1 and 10, inclusive;

$R_2'$, $R_3'$, $R_4'$, $R_5'$, and $R_6'$ comprise, each independently, H, an alkyl group, an alkenyl group, an alkynyl group, an aromatic group, a heterocyclic group, or a part of a ring group, such as cycloalkyl groups, heterocyclic groups, and a benzo group; and Q' is O, S, or $NR_7$ where $R_7$ is H, an alkyl group, an acyl group, an alkenyl group, an alkynyl group, a heterocyclic group, or an aromatic group.

In further embodiments of interest, when $R_1$ of Formula (I) comprises a heterocycle hydrazone group of Formula (II), X of Formula (I) may have the formula:

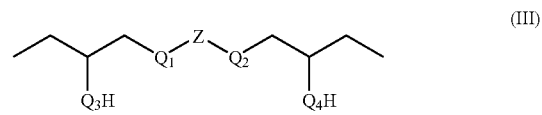

(III)

where $Q_1$, $Q_2$, $Q_3$, and $Q_4$ are, each independently, O, S, or $NR_8$; Z comprises a bond, an alkylene group, an aromatic group, a heterocyclic group, or a combination thereof; and $R_8$ is H, an alkyl group, an acyl group, an alkenyl group, an alkynyl group, a heterocyclic group, or an aromatic group. In some embodiments of interest, $Q_1$ and $Q_2$ are each S, $Q_3$ and $Q_4$ are each O, and Z is selected from the group consisting of the formulae:

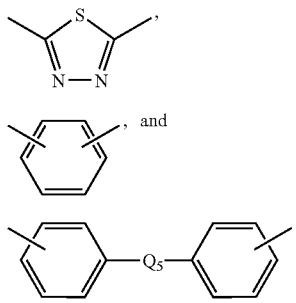

(IV), (V), and (VI)

where $Q_5$ is a bond, O, S, or $NR_9$, and $R_9$ is H, an alkyl group, an acyl group, an alkenyl group, an alkynyl group, a heterocyclic group, or an aromatic group.

The $R_6$ group of Formula (I) and the $R_6'$ groups of Formula (II) may be in either 2- or 3-position of the corresponding 5-membered heterocyclic ring. Similarly, the hydrazone groups of Formula (I) and Formula (II) may be in either 2- or 3-position of the corresponding 5-membered heterocyclic ring. Furthermore, $R_4$ and $R_5$ together may form an aliphatic or aromatic ring fused with the corresponding 5-membered heterocyclic ring. Similarly, $R_4'$ and $R_5'$ together, $R_5$ and $R_6$ together, and $R_5'$ and $R_6'$ together may form an aliphatic or aromatic ring fused with the corresponding 5-membered heterocyclic ring.

Specific, non-limiting examples of suitable charge transport materials within Formula (I) of the present invention include the following structures:

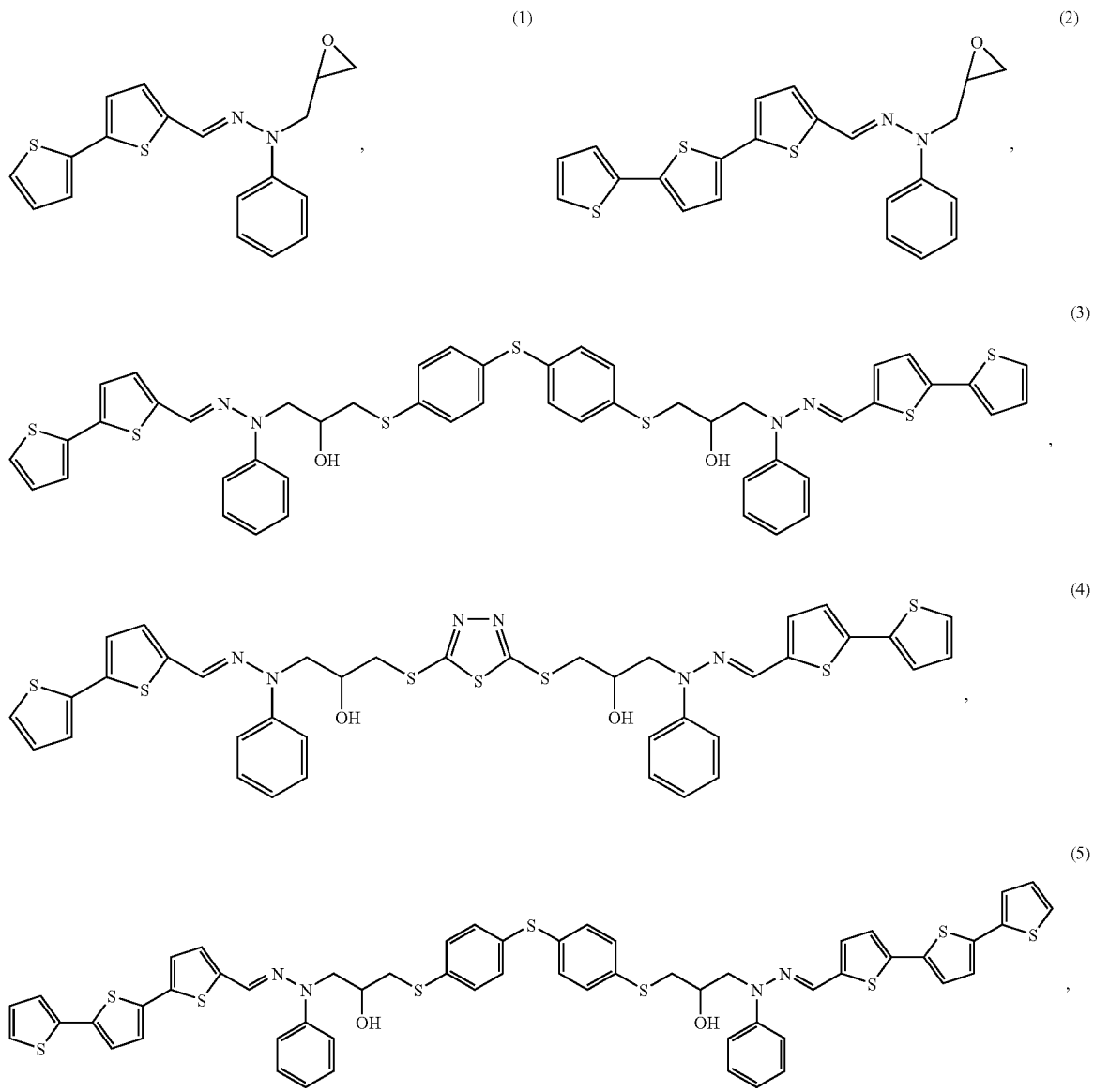

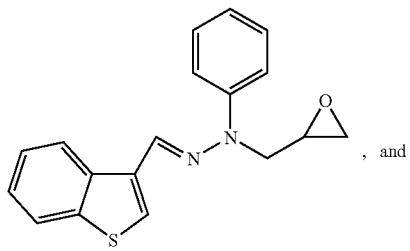

, and

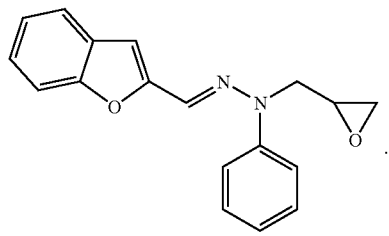

Each of Compounds (1)-(7) and Formulae (I)-(VI) above may further comprise at least a substituent. Non-limiting examples of suitable substituent include a hydroxyl group, a thiol group, a carboxyl group, an amino group, a halogen, an alkyl group, an acyl group, an alkoxy group, an alkylsulfanyl group, an alkenyl group, an alkynyl group, an ester group, an amido group, a nitro group, a cyano group, a sulfonate group, a phosphate, phosphonate, a heterocyclic group, an aromatic group, a hydrazone group, an enamine group, an azine group, an epoxy group, a thiiranyl group, and an aziridinyl group.

Synthesis of Charge Transport Materials

The synthesis of the charge transport materials of this invention can be prepared by the following multi-step synthetic procedures, although other suitable procedures can be used by a person of ordinary skill in the art based on the disclosure herein.

General Synthetic Procedure A for Charge Transport Materials of Formula (I)

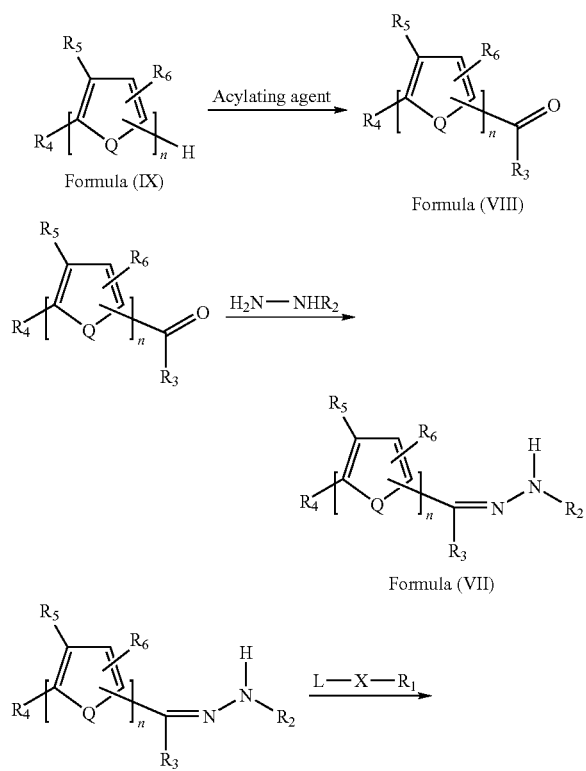

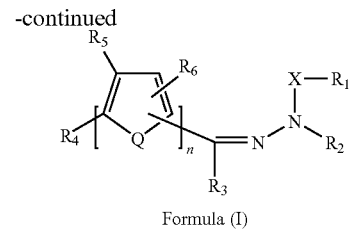

Formula (I)

The acylated heterocycle of Formula (VIII) may be prepared by reacting the corresponding heterocycle of Formula (IX) with an acylating agent to substitute one hydrogen in the heterocycle with an acyl group ($R_3CO$). The $R_4$, $R_5$, and $R_6$ groups of the heterocycle of Formula (IX) comprise, each independently, H, an alkyl group, an alkenyl group, an alkynyl group, an aromatic group, a heterocyclic group, or a part of a ring group, such as cycloalkyl groups, heterocyclic groups, or a benzo group; and Q comprises O, S, or NR where R is H, an alkyl group, an acyl group, an alkenyl group, an alkynyl group, a heterocyclic group, or an aromatic group.

Depending on the acylating agent, $R_3$ may comprise H, an alkyl group, an alkenyl group, an alkynyl group, an aromatic group, a heterocyclic group, or a part of a ring group, such as cycloalkyl groups, heterocyclic groups, or a benzo group. The acylation of the heterocycle of Formula (IX) may be done with a mixture of a Lewis acid such as tin tetrachloride and dichloromethyl methyl ether. Alternatively, the acylation of the heterocycle of Formula (IX) may be done under Vilsmeier-Haack condition with a mixture of phosphorus oxychloride ($POCl_3$) and an N,N-dialkylamide, such as N,N-dimethylformamide, N,N-dimethylacetamide, and N,N-dimethylbenzamide. Alternatively, the heterocycle of Formula (IX) may be acylated by a mixture of a strong base, such as butyl lithium, and an N,N-dialkylamide, or by a mixture of Lewis acid, such as stannic chloride, and an acid anhydride, such as acetic anhydride at an elevated temperature. The C-acylations of aromatic hetercycles such as thiophenes, furans, and pyrroles under Vilsmeier-Haack condition are described in Alan Katritzky, "Handbook of heterocyclic chemistry," Pergamon Press, New York, p. 254-255 (1985), which is incorporated herein by reference. Furthermore, the Vilsmeier-Haack acylation and related reactions are described in Carey et al., "Advanced Organic Chemistry, Part B: Reactions and Synthesis," New York, 1983, pp. 380-393, which is incorporated herein by reference.

When $R_3$ of Formula (VIII) is H, the formyl derivative of the heterocycle of Formula (IX) may be prepared by the photoformylation reaction of the heterocycle of Formula (IX) in chloroform. The photoformylation reaction is described in Chowdhury et al., *Indian Journal of Chemistry, Section B:*

*Organic Chemistry Including Medicinal Chemistry*, Vol. 29B (5), pp. 405-6 (1990), which is incorporated herein by reference. Alternatively, the formyl derivative of the heterocycle of Formula (IX) may be prepared by oxidizing the corresponding methyl derivative of the heterocycle of Formula (IX) either photochemically or with 2,3-dichloro-5,6-dicyanobenzoquinone. The photochemical oxidation reaction is described in Chowdhury et al., *Chemistry & Industry*, Vol. 4, pp. 128-9 (1987), which is incorporated herein by reference. The oxidation reaction with 2,3-dichloro-5,6-dicyanobenzoquinone is described in Anwer et al., *Indian Journal of Chemistry*, Vol. 11(12), pp. 1314-15 (1973), which is incorporated herein by reference.

The heterocycle hydrazone of Formula (VII) may be prepared by reacting the acylated heterocycle of Formula (VIII) with a hydrazine, $H_2N-NHR_2$ where $R_2$ comprises H, an alkyl group, an alkenyl group, an aromatic group group, a heterocyclic group, or a part of a ring group, such as cycloalkyl groups, heterocyclic groups, or a benzo group. The hydrazone formation reaction may take place in a solvent, such as tetrahydrofuran and methanol. The hydrazone formation reaction may be catalyzed by an appropriate amount of acid, such as acetic acid, sulfuric acid and hydrochloric acid. The reaction mixture may be heated at an elevated temperature for a period of time, such as 2 to 14 hours. The heterocycle hydrazone of Formula (VII) may be isolated and purified by conventional purification techniques, such as chromatography and recrystallization.

The charge transport material of Formula (I) may be prepared by reacting the heterocycle hydrazone of Formula (VII) with $L-X-R_1$ where $R_1$ comprises a reactive ring group, such as an epoxy group, a thiiranyl group, an aziridinyl group, and an oxetanyl group, an ethylenically unsaturated group, such as a vinyl ether group, an alkenyl group, an acryloyl group, a methacryloyl group, an acrylamido group, and a methacrylamido group, a reactive polar group, such as a hydroxyl group, a thiol group, a carboxyl group, and an amino group, an azine group, or a hydrazone group; X is a bond or a linking group, such as a $-(CH_2)_m-$ group, where m is an integer between 1 and 10, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen. In some embodiments, the X group comprises a bond, an alkylene group, such as methylene and ethylene, or $-(CH_2)_pO-$ group where p is an integer between 1 and 10. The L group is a good leaving group such as halides (e.g., fluoride, chloride, bromide, and iodide), mesylate and tosylate.

The above substitution reaction may take place in a solvent, such as ethyl methyl ketone and tetrahydrofuran. The substitution reaction may be catalyzed by a base, such as potassium hydroxide, potassium carbonate, and a combination thereof. The reaction mixture may be heated at an elevated temperature for a period of time, such as 2 to 48 hours. When the reaction is completed, the charge transport material of Formula (I) may be isolated and purified by conventional purification techniques, such as chromatography and recrystallization.

Some non-limiting examples of $L-X-R_1$ include vinyl chloroformate, isopropenyl chloroformate, vinyl chloroacetate, 2-chloroethyl vinyl ether, 6-(vinyloxy)-1-hexyl mesylate, 4-(vinyloxy)-1-butyl mesylate, 2-(vinyloxy)ethyl mesylate, 6-(vinyloxy)-1-hexyl tosylate, 4-(vinyloxy)-1-butyl tosylate, and 2-(vinyloxy)ethyl tosylate. The mesylates and tosylates can be prepared by the reaction between 6-(vinyloxy)-1-hexanol, 1,4-butanediol vinyl ether, and 2-(vinyloxy)ethanol with mesyl chloride and tosyl chloride respectively. The above-mentioned chemicals may be obtained commercially from a supplier such as Aldrich, Milwaukee, Wis.

Other non-limiting examples of $L-X-R_1$ include methacryloyl chloride, acryloyl chloride, crotonoyl chloride, 3-dimethylacryloyl chloride, cinnamoyl chloride, 2,6,6-trimethyl-1-cyclohexene-1-carbonyl chloride, 2,3,3-trichloroacryloyl chloride, 3-(2-chlorophenyl)-2-propenoyl chloride, 4-nitrocinnamoyl chloride, 3-(trifluoromethyl)cinnamoyl chloride, 2-[(dimethylamino)methylene]malonoyl dibromide, all of which may be obtained from commercial suppliers such as Aldrich.

Further non-limiting examples of $L-X-R_1$ include compounds having a reactive ring group. The reactive ring group may be selected from the group consisting of heterocyclic ring groups that have a higher strain energy than their corresponding open-ring structures. The conventional definition of strain energy is that it represents the difference in energy between the actual molecule and a completely strain-free molecule of the same constitution. More information about the origin of strain energy can be found in the article by Wiberg et al., "A Theoretical Analysis of Hydrocarbon Properties: II Additivity of Group Properties and the Origin of Strain Energy," *J. Am. Chem. Soc.* 109, 985 (1987), which is incorporated herein by reference. The heterocyclic ring group may have 3, 4, 5, 7, 8, 9, 10, 11, or 12 members, in further embodiments 3, 4, 5, 7, or 8 members, in some embodiments 3, 4, or 8 members, and in additional embodiments 3 or 4 members. Non-limiting examples of such heterocyclic ring are cyclic ethers (e.g., epoxides and oxetane), cyclic amines (e.g., aziridine), cyclic sulfides (e.g., thiirane), cyclic amides (e.g., 2-azetidinone, 2-pyrrolidone, 2-piperidone, caprolactam, enantholactam, and capryllactam), N-carboxy-α-amino acid anhydrides, lactones, and cyclosiloxanes. The chemistry of the above heterocyclic rings is described in George Odian, "Principle of Polymerization," second edition, Chapter 7, p. 508-552 (1981), which is incorporated herein by reference.

In some embodiments of interest, the reactive ring group is an epoxy group. A diamino-aromatic heterocyclic compound having an epoxy group may be prepared by reacting a corresponding compound with an organic halide comprising an epoxy group. Non-limiting examples of suitable organic halide comprising an epoxy group as the reactive ring group are epihalohydrins, such as epichlorohydrin. The organic halide comprising an epoxy group can also be prepared by the epoxidation reaction of the corresponding alkene having a halide group. Such epoxidation reaction is described in Carey et al., "Advanced Organic Chemistry, Part B: Reactions and Synthesis," New York, 1983, pp. 494-498, incorporated herein by reference. The alkene having a halide group can be prepared by the Wittig reaction between a suitable aldehyde or keto compound and a suitable Wittig reagent. The Wittig and related reactions are described in Carey et al., "Advanced Organic Chemistry, Part B: Reactions and Synthesis," New York, 1983, pp. 69-77, which is incorporated herein by reference.

In other embodiments of interest, the reactive ring group is a thiiranyl group. A diamino-aromatic heterocyclic compound having an epoxy group, such as those described above, can be converted into the corresponding thiiranyl compound by refluxing the epoxy compound and ammonium thiocyanate in tetrahydrofuran. Alternatively, the corresponding thiiranyl compound may be obtained by passing a solution of the above-described epoxy compound through 3-(thiocyano)propyl-functionalized silica gel (commercially available form Aldrich, Milwaukee, Wis.). Alternatively, a thiiranyl compound may be obtained by the thia-Payne rearrangement of a corresponding epoxy compound. The thia-Payne rearrangement is described in Rayner, C. M. Synlett 1997, 11; Liu, Q. Y.; Marchington, A. P.; Rayner, C. M. Tetrahedron 1997, 53, 15729; Ibuka, T. Chem. Soc. Rev. 1998, 27, 145; and Rayner, C. M. Contemporary Organic Synthesis 1996, 3, 499. All the above four articles are incorporated herein by reference.

In other embodiments of interest, the reactive ring group is an aziridinyl group. An aziridine compound may be obtained by the aza-Payne rearrangement of a corresponding diamino-aromatic heterocyclic compound having an epoxy group, such as one of those epoxy compounds described above. The thia-Payne rearrangement is described in Rayner, C. M. Synlett 1997, 11; Liu, Q. Y.; Marchington, A. P.; Rayner, C. M. Tetrahedron 1997, 53, 15729; and Ibuka, T. Chem. Soc. Rev. 1998, 27, 145. All the above three articles are incorporated herein by reference. Alternatively, an aziridine compound may be prepared by the addition reaction between a suitable nitrene compound and a suitable alkene. Such addition reaction is described in Carey et al., "Advanced Organic Chemistry, Part B: Reactions and Synthesis," New York, 1983, pp. 446-448, incorporated herein by reference.

In further embodiments of interest, the reactive ring group is an oxetanyl group. An oxetane compound may be prepared by the Paterno-Buchi reaction between a suitable carbonyl compound and a suitable alkene. The Paterno-Buchi reaction is described in Carey et al., "Advanced Organic Chemistry, Part B: Reactions and Synthesis," New York, 1983, pp. 335-336, which is incorporated herein by reference. 3-Chloromethyl-3-alkyloxetanes may be prepared according to the procedure disclosed in Japanese Publication No. 10-212282, which is incorporated herein by reference.

In additional examples, the reactive ring may be a 5 or 7-membered ring comprising a —COO— group or a —CONR— group, such as butyrolactone, N-methylbutyrolactam, N-methylcaprolactam, and caprolactone.

General Synthetic Procedure B for Bridged Charge Transport Materials of Formula (I) Where $R_1$ Comprises A Hydrazone Group) Having Formula (II)

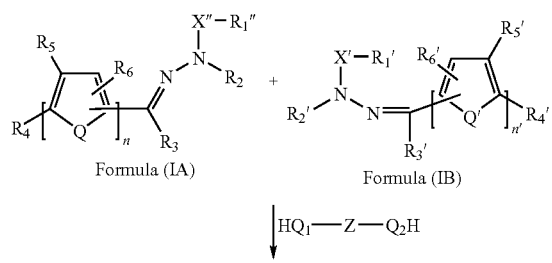

Formula (IA)    Formula (IB)

$HQ_1\text{—}Z\text{—}Q_2H$

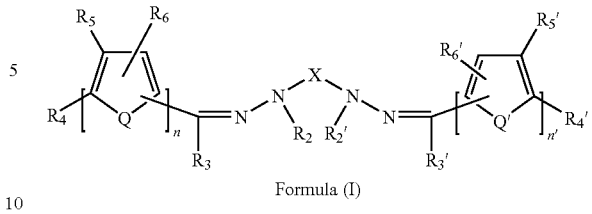

Formula (I)

In some embodiments, the bridged charge transport materials of Formula (I) where $R_1$ comprises a hydrazone group having Formula (II) may be prepared by reacting a bridging compound having the formula $HQ_1$-Z-$Q_2$H with a compound of Formula (IA) and a compound of Formula (IB) either simultaneously or sequentially, where Z is a bridging group; Q and Q' are, each independently, O, S, or NR where R is H, an alkyl group, an acyl group, an alkenyl group, an alkynyl group, a heterocyclic group, or an aromatic group; $R_1$' and $R_1$" are each a group, such as a reactive ring group, that is reactive towards the $HQ_1$- and $HQ_2$-groups of the bridging compound; $R_2$, $R_3$, $R_4$, $R_5$, $R_6$, $R_2$, $R_3$, $R_4$, $R_5$, and $R_6$ comprise, each independently, H, an alkyl group, an alkenyl group, an alkynyl group, an aromatic group, a heterocyclic group, or a part of a ring group, such as cycloalkyl groups, heterocyclic groups, or a benzo group; and X' and X" are each a linking group.

Z, X', and X" may be each a $—(CH_2)_m—$ group, where m is an integer between 1 and 20, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen.

X is the reaction product of X"—$R_1$", $HQ_1$-Z-$Q_2$H, and X'—$R_1$'. In some embodiments, when X' and X" are each a methylene group; and $R_1$' and $R_1$" are each an epoxy group, X has the formula:

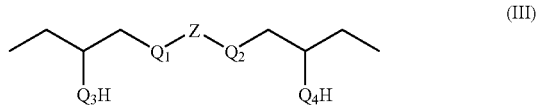

where $Q_1$, $Q_2$, $Q_3$, and $Q_4$ are, each independently, O, S, or $NR_8$; Z comprises a bond, an alkylene group, an aromatic group, a heterocyclic group, or a combination thereof; and $R_8$ is H, an alkyl group, an acyl group, an alkenyl group, an alkynyl group, a heterocyclic group, or an aromatic group.

Both the compound of Formula (IA) and the compound of Formula (IB) may be prepared by the general synthetic procedure A mentioned above. The reaction may be catalyzed by an organic base such as triethylamine. The compound of Formula (IA) and the compound of Formula (IB) may be the same or different. The bridged charge transport materials of Formula (I) are symmetrical if the compound of Formula (IA) and the compound of Formula (IB) are the same and $HQ_1$-Z-$Q_2H$ is symmetrical. The bridged charge transport materials of Formula (I) are unsymmetrical if the compound of Formula (IA) and the compound of Formula (IB) are different or $HQ_1$-Z-$Q_2H$ is unsymmetrical. When Formula (IA) is the same as Formula (IB), the bridging compound may react with Formula (IA) and Formula (IB) in one step. When Formula (IA) is different than Formula (IB), the bridging compound may react with Formula (IA) and Formula (IB) sequentially.

In some embodiments, the bridging compound may be a diol, a dithiol, a diamine, a dicarboxylic acid, a hydroxylamine, an amino acid, a hydroxyl acid, a thiol acid, a hydroxythiol, or a thioamine. Non-limiting examples of suitable dithiol are 3,6-dioxa-1,8-octanedithiol, erythro-1,4-dimercapto-2,3-butanediol, (±)-threo-1,4-dimercapto-2,3-butanediol, 4,4'-thiobisbenzenethiol, 1,4-benzenedithiol, 1,3-benzenedithiol, sulfonyl-bis(benzenethiol), 2,5-dimecapto-1,3,4-thiadiazole, 1,2-ethanedithiol, 1,3-propanedithiol, 1,4-butanedithiol, 2,3-butanedithiol, 1,5-pentanedithiol, and 1,6-hexanedithiol. Non-limiting examples of suitable diols are 2,2'-bi-7-naphtol, 1,4-dihydroxybenzene, 1,3-dihydroxybenzene, 10,10-bis(4-hydroxyphenyl)anthrone, 4,4'-sulfonyldiphenol, bisphenol, 4,4'-(9-fluorenylidene)diphenol, 1,10-decanediol, 1,5-pentanediol, diethylene glycol, 4,4'-(9-fluorenylidene)-bis(2-phenoxyethanol), bis(2-hydroxyethyl)terephthalate, bis[4-(2-hydroxyethoxy)phenyl]sulfone, hydroquinone-bis(2-hydroxyethyl)ether, and bis(2-hydroxyethyl)piperazine. Non-limiting examples of suitable diamine are diaminoarenes, and diaminoalkanes. Non-limiting examples of suitable dicarboxylic acid are phthalic acid, terephthalic acid, adipic acid, and 4,4'-biphenyldicarboxylic acid. Non-limiting examples of suitable hydroxylamine are p-aminophenol and fluoresceinamine. Non-limiting examples of suitable amino acid are 4-aminobutyric acid, phenylalanine, and 4-aminobenzoic acid. Non-limiting examples of suitable hydroxyl acid are salicylic acid, 4-hydroxybutyric acid, and 4-hydroxybenzoic acid. Non-limiting examples of suitable hydroxythiol are monothiohydroquinone and 4-mercapto-1-butanol. Non-limiting example of suitable thioamine is p-aminobenzenethiol. Non-limiting example of suitable thiol acid are 4-mercaptobenzoic acid and 4-mercaptobutyric acid. Almost all of the above bridging compounds are available commercially from Aldrich and other chemical suppliers.

In further embodiments of interest, Z may be selected from the group consisting of the formulae:

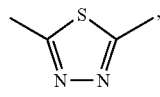
(IV)

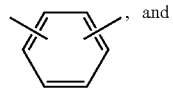
(V)

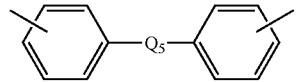
(VI)

where $Q_5$ is a bond, O, S, or $NR_9$, and $R_9$ is H, an alkyl group, an acyl group, an alkenyl group, an alkynyl group, a heterocyclic group, or an aromatic group.

In other embodiments, the bridged charge transport materials of Formula (I) may be prepared by reacting a compound of Formula (IA) with a compound of Formula (IB) where $R_1'$ comprises a reactive ring group (or a reactive polar group) and $R_2''$ comprises a reactive polar group (or a reactive ring group). The reaction between the reactive ring group and the reactive polar group may be catalyzed by an organic base such as triethylamine. In further embodiments of interest, the charge transport materials of Formula (I) where Y The invention will now be described further by way of the following examples.

EXAMPLES

Example 1

Synthesis and Characterization Charge Transport Materials

This example describes the synthesis and characterization of Compounds (1)-(7) in which the numbers refer to formula numbers above. The characterization involves chemical characterization of the compositions. The electrostatic characterization, such as mobility and ionization potential, of the materials formed with the compositions is presented in a subsequent example.

Synthesis of 2,2'-bithiophene-5-carboxaldehyde N-phenylhydrazone

A mixture of 2,2'-bithiophene-5-carboxaldehyde (5.0 g, 0.0257 mole, obtained from TCI Europe nv, Boerenveldseweg 6, 2070 Zwijndrecht) and 10 ml of 2-propanol was added to a 100 ml, 2 neck round bottom flask equipped with a reflux condenser and a mechanical stirrer. Heat was applied until all 2,2'-bithiophene-5-carboxaldehyde entered into solution. After all 2,2'-bithiophene-5-carboxaldehyde was dissolved, a hot solution of phenylhydrazine (3.05 g, 2.78 ml, 0.0309 mole, obtained from Aldrich) in 3 ml of 2-propanol was added to the 2,2'-bithiophene-5-carboxaldehyde solution. After the reaction mixture was refluxed for 6 hours, the mixture was cooled to room temperature. The crystals formed were filtered off, and then washed with a mixture of 2-propanol and hexane in 1:1 ratio by volume. The yield of the product, 2,2'-bithiophene-5-carboxaldehyde N-phenylhydrazone, was 6.95 g (94.9%). The product was recrystallized from 2-propanol and dried at 60° C. in a vacuum oven for 6 hours. The melting point of the product was found to be 156-158° C. An infrared absorption spectrum of the product was characterized by the following absorption wave numbers (KBr window, cm$^{-1}$): 3306 (NH); 3104, 3061 (CH$_{aromatic}$); 1599 (C=C, C—N). A $^1$H-NMR spectrum (300 MHz) of the product in CDCl$_3$ was characterized by the following chemical shifts (δ, ppm): 7.77 (s, 1H, CH=N); 7.30-7.00 (m, 9H, Ph, Ht, NH); 6.95 (d, 1H, Ht); 6.87 (t, 1H, 4-H Ph). An elemental analysis yielded the following results in weight percent: C, 63.50; H, 4.16; N, 9.97, which compares with the following calculated elemental weight percent for a compound with the formula $C_{15}H_{12}N_2S_2$: C, 63.35; H, 4.25; N, 9.85.

Synthesis of 9-Ethyl-3-Carbazolecarboxaldehyde N-(2,3-Epoxypropyl)-N-Phenylhydrazone 9-Ethyl-3-carbazolecarboxaldehyde N-Phenylhydrazone. After 9-ethylcarbazole-3-carbaldehyde (10 g, 0.045 mol, from Aldrich, Milwaukee, Wis.) was dissolved in 300 ml of methanol under mild heating, a solution of 7.25 g (0.067 mol) of N-phenylhydrazine (obtained from Aldrich) in methanol was added. The reaction mixture was refluxed for 2 hours.

Yellowish crystals were separated by filtration, washed with a large amount of methanol, and dried. The yield of the product, 9-ethyl-3-carbazolecarboxaldehyde N-phenylhydrazone, was 13.12 g (92%). The melting point of the product was found to be 136-137° C. The $^1$H-NMR spectrum (100 MHz) of the product in CDCl$_3$ was characterized by the following chemical shifts (δ, ppm): 1.34 (t, J=7.0 Hz, 3H, CH$_3$); 4.23 (q, J=7.0 Hz, 2H, CH$_2$); 6.90-7.64 (m, 8H, Ar); 7.60 (s, 1H, Ar); 7.81 (dd, 1H, Ar); 8.08 (d, 2H, Ar); and 8.15(d, 1H, =CH). The infrared absorption spectrum of the product was characterized by the following the following absorption wave numbers (KBr windows, in cm$^{-1}$): ν(N—H) 3306, ν(C—H) 2972, ν(arene C—H) 3051, ν(C=C, C—N in Ar) 1602; 1494; 1475; 1237, ν(C—N) 1256, γ(Ar) 815; 747; 731. The mass spectrum of the product was characterized by the following ions (in m/z): 314 (90%, M+1); 222 (100%, H$_5$C$_2$-C$_{12}$H$_7$N—CH=NH).

A mixture of potassium hydroxide powder (KOH, 85%, 198 g, 3 mol) and anhydrous sodium sulfate (Na$_2$SO$_4$, 51 g, 0.369 mol) was added in three stages to a mixture of 9-ethyl-3-carbazolecarboxaldehyde N-phenylhydrazone (313.4 g, 1 mol) and epichlorohydrin (1.5 mol, from Aldrich, Milwaukee, Wis.), while keeping the reaction mixture at 20-25° C. In the first stage, 33 g of Na$_2$SO$_4$ and 66 g of KOH were added initially. In the second stage, 9.9 g of Na$_2$SO$_4$ and 66 g of KOH were added 1 hour into the reaction. In the third stage, 9.9 g of Na$_2$SO$_4$ and 66 g of KOH were added 2 hours into the reaction. The reaction mixture was stirred vigorously at 35-40° C. until the starting hydrazone disappeared (approximately 3-4 hours). Subsequently, the mixture was cooled to room temperature and any remaining solids were removed by filtration. The liquid organic phase was treated with diethyl ether and washed with distilled water until the washed water had a neutral pH. The organic layer was dried over anhydrous magnesium sulfate, treated with activated charcoal, and filtered. The solvent and excess epichlorohydrin were removed by evaporation in a rotary evaporator. The residue was recrystallized from a mixture of toluene and 2-propanol in a 1:1 volume ratio. The crystals formed upon standing were filtered off and washed with 2-propanol to give 290 g of product (78.5% yield). The melting point of the product was found to be 136-137° C. (recrystallized from toluene). The $^1$H-NMR spectrum (250 MHz) of the product in CDCl$_3$ was characterized by the following chemical shifts (δ, ppm): 8.35 (s, 1H, 4-H$_{Ht}$); 8.14 (d, J=7.8 Hz, 1H, 1-H$_{Ht}$); 7.93 (d, J=7.6 Hz, 1H, 2-H$_{Ht}$); 7.90 (s, 1H, CH=N); 7.54-7.20 (m, 8H, Ph, Ht); 6.96 (t, J=7.2 Hz, 1H, 4-H$_{Ph}$); 4.37 (m, 3H, C$\underline{H}_2$CH$_3$, one of the NCH$_2$ protons); 4.04 (dd, J$_1$=4.3 Hz, J$_2$=16.4 Hz, 1H, next of the NCH$_2$ protons); 3.32 (m, 1H, CH); 2.88 (dd, 1H, part of the ABX system, cis-H$_A$ of CH$_2$O, J$_{AX}$=2.6 Hz, J$_{AB}$=4.9 Hz); 2.69 (dd, 1H, part of the ABX system, trans-H$_B$ of CH$_2$O, J$_{BX}$=4.0 Hz); and 1.44 (t, J=7.2 Hz, 3H, CH$_3$). An elemental analysis yielded the following results in weight percent C 78.32, H 6.41, and N 11.55, which compared with calculated values for C$_{24}$H$_{23}$N$_3$O in weight percent of C 78.02, H 6.28, and N 11.37.

Compound (1)

Compound (1), 2,2'-bithiophene-5-carboxaldehyde N-2,3-epoxypropyl-N-phenylhydrazone, was prepared according to the procedure above for 9-ethyl-3-carbazolecarbaldehyde N-2,3-epoxypropyl-N-phenylhydrazone except that 9-ethyl-3-carbazolecarbaldehyde phenylhydrazone was replaced by 2,2'-bithiophene-5-carboxaldehyde phenylhydrazone 6.7 g (0.0236 mole). The product was purified by column chromatography (silica gel, grade 62, 60-200 mesh, 150 Å, from Aldrich, Milwaukee, Wis.) using an eluant mixture of ethyl acetate and hexane in a volume ratio of 1:5 to obtain 5.75 g (61%) of the product. The product was recrystallized from diethyl ether and dried at 30° C. in a vacuum oven for 5 hours. The melting point of the product was found to be 85-86.5° C. An infrared absorption spectrum of the product was characterized by the following absorption wave numbers (KBr window, cm$^{-1}$): 3098, 3061 (CH$_{aromatic}$); 2988, 2912 (CH$_{aliphatic}$); 1595, 1568 (C=C, C—N); 751, 695 (CH=CH of monosubstituted benzene). A $^1$H-NMR spectrum (300 MHz) of the product in CDCl$_3$ was characterized by the following chemical shifts (δ, ppm): 7.77 (s, 1H, CH=N); 7.40-6.93 (m, 8H, Ph, Ht); 7.06 (d, 1H, Ht); 7.04 (d, 1H, Ht); 4.32 (dd, 1H, part of ABX system, cis-H$_B$ of NCH$_2$, J$_{BX}$=2.1 Hz); 3.88 (dd, 1H, part of ABX system, trans-H$_A$ of NCH$_2$, J$_{AX}$=5.1 Hz, J$_{AB}$=16.5 Hz); 3.24 (m, 1H, CH); 2.84 (dd, 1H, part of ABX system, trans-H$_A$ of OCH$_2$, J$_{AX}$=3.9 Hz, J$_{AB}$=4.8 Hz); 2.62 (dd, 1H, part of ABX system, cis-H$_B$ of OCH$_2$, J$_{BX}$=2.7 Hz). An elemental analysis yielded the following results in weight percent: C, 63.61; H, 4.66; N, 8.57, which compares with the following calculated elemental weight percent for a compound with the formula C$_{18}$H$_{16}$N$_2$OS$_2$: C, 63.50; H, 4.74; N, 8.23.

Compound (2)

Compound (2) was prepared according to the preparation procedure above for Compound (1) except that 9-ethyl-3-carbazolecarbaldehyde phenylhydrazone was replaced by 2,2':5',2"-tertiophene-5-carboxaldehyde N-phenylhydrazone (2.5 g, 7.01 mmole), which was prepared according to the preparation procedure above for 2,2'-bithiophene-5-carboxaldehyde N-phenylhydrazone except that 2,2'-bithiophene-5-carboxaldehyde was replaced by 2,2':5',2"-tertiophene-5-carboxaldehyde (2 g, 7.24 mmole, obtained from TCI Europe nv, Boerenveldseweg 6, 2070 Zwijndrecht). The product was purified by column chromatography using a column packed with silica gel (grade 62, 60-200 mesh, 150 Å, Aldrich) and an eluant mixture of ethyl acetate and hexane in 1:4 ratio by volume. The yield of the product was 1.56 g (52.7%). The melting point of the product was found to be 107-108.5° C. An infrared absorption spectrum of the product was characterized by the following absorption wave numbers (KBr window, cm$^{-1}$): 3062 (arom. CH); 2978 (aliph. CH); 1263, 1234, 936, 836 (epoxy group); 791, 740, 684 (CH=CH of monosubstituted benzene and thiophene). An elemental analysis yielded the following results in weight percent: C, 64.72; H, 4.56; N, 3.58, which compares with the following calculated elemental weight percent for a compound with the formula C$_{22}$H$_{19}$NOS$_3$: C, 64.51; H, 4.68; N, 3.42.

Compound (3)

After 4,4'-thiobisbenzenethiol (98%, 0.72 g, 2.88 mmol, obtained from Aldrich, Milwaukee, Wis.) was dissolved in 6 ml butanone, Compound (1) (2.45 g, 7.2 mmole) and the triethylamine (0.29 g, 4 ml, 2.88 mmol, obtained from Aldrich) were added. The reaction mixture was stirred at room temperature for 36 hours. After the completion of the reaction (Confirmed by TLC with an eluant mixture of ethyl acetate and hexane in a volume ratio of 1:2.6), butanone was removed and the product was purified by column chromatography using a column packed with silica gel (grade 62, 60-200 mesh, 150 Å, commercially obtained from Aldrich, Milwaukee, Wis.) and an eluant mixture of acetone and hexane in a volume ratio of 1:5. Fractions containing the product were collected and the eluant was evaporated. The yield of the product was 1.8 g (53.7%). An infrared absorption spectrum of the product was characterized by the following absorption wave numbers (KBr window, cm$^{-1}$): 3416 (OH, broad); 3102, 3064 (CH$_{aromatic}$); 2956, 2920 (CH$_{aliphatic}$); 1596, 1569

(C=C, C—N); 751, 693 (CH=CH of monosubstituted benzene). A $^1$H-NMR spectrum (300 MHz) of the product in CDCl$_3$ was characterized by the following chemical shifts (δ, ppm): 7.67 (s, 2H, CH=N); 7.36-6.78 (m, 26H, Ph, Ht); 6.84 (m, 2H, 4-H Ph); 4.21-4.13 (m, 2H, CH); 4.06 (dd, 2H, part of ABX system, cis-H$_B$ of NCH$_2$, J$_{BX}$=4.2 Hz); 3.97 (dd, 2H, part of ABX system, trans-H$_A$ of NCH$_2$, J$_{AX}$=7.2 Hz, J$_{AB}$=15.3 Hz); 3.14 (dd, 2H, part of ABX system, cis-HA of SCH$_2$, J$_{AX}$=5.7 Hz, J$_{AB}$=13.8 Hz); 3.07 (dd, 2H, part of ABX system, trans-HB of SCH$_2$, J$_{BX}$=6.9 Hz); 3.07-2.8 (m, 1H, OH). An elemental analysis yielded the following results in weight percent: C, 61.71; H, 4.66; N, 6.27, which compares with the following calculated elemental weight percent for a compound with the formula C$_{48}$H$_{42}$N$_4$O$_2$S$_7$: C, 61.90; H, 4.55; N 6.02.

Compound (4)

Compound (4) was prepared according to the preparation procedure for Compound (3) except that 4,4'-thiobisbenzenethiol was replaced by 2,5-dimercapto-1,3,4-thiadiazole (0.424 g, 2.82 mmole, obtained from Aldrich, Milwaukee, Wis.). The yield of the product was 1.36 g (58.1%). An infrared absorption spectrum of the product was characterized by the following absorption wave numbers (KBr window, cm$^{-1}$): 3616-3074 (OH, broad); 3103, 3066 (CH$_{aromatic}$); 2979, 2923 (CH$_{aliphatic}$); 1596, 1569 (C=C, C—N); 751, 693 (CH=CH of monosubstituted benzene). A $^1$H-NMR spectrum (300 MHz) of the product in CDCl$_3$ was characterized by the following chemical shifts (δ, ppm): 7.73 (s, 2H, CH=N); 7.35-6.92 (m, 20H, Ph, Ht); 4.48-4.35 (m, 2H, CH); 4.07-3.90 (m, 6H, NCH$_2$, OH); 3.60-3.26 (m, 4H, SCH$_2$). An elemental analysis yielded the following results in weight percent: C, 54.71; H, 4.26; N, 10.27, which compares with the following calculated elemental weight percent for a compound with the formula C$_{38}$H$_{34}$N$_6$O$_2$S$_7$: C, 61.90; H, 4.55; N, 6.02.

Compound (5)

Compound (5) was prepared according to the preparation procedure above for Compound (3) except that Compound (1) was replaced by Compound (2) (1.56 g, 3.552 mmole). The yield of the product was 1.0 g (75%). The product was recrystallized from toluene. An infrared absorption spectrum of the product was characterized by the following absorption wave numbers (KBr window, cm$^{-1}$): 3439 (OH broad); 3062 (arom. CH); 2965, 2914 (aliph. CH); 788, 748, 690 (CH=CH of monosubstituted benzene and thiophene). A $^1$H-NMR spectrum (300 MHz) of the product in DMSO-d$_6$ was characterized by the following chemical shifts (δ, ppm): 7.97, 7.96 (two s, 2H, CH=N); δ=7.50 (d, 2H, CH of 2,2':5',2''-tertiophene); 7.46-6.83 (m, 28H, CH of 2,2':5',2''-tertiophene and Ar); δ=6.87 (m, 2H, 4-H Ph); δ=5.56 (d, 2H, OH); δ=4.20-3.96 (m, 6H, NCH$_2$CH); δ=3.28-3.10 (m, 4H, SCH$_2$). An elemental analysis yielded the following results in weight percent: C, 61.41; H, 5.23; N, 5.37, which compares with the following calculated elemental weight percent for a compound with the formula C$_{56}$H$_{46}$N$_4$O$_2$S$_9$: C, 61.39; H, 4.23; N, 5.11.

Compound (6)

Compound (6) may be prepared according to the preparation procedure above for Compound (1) except that 9-ethyl-3-carbazolecarbaldehyde phenylhydrazone is replaced by 1-benzothiophene-3-carbaldehyde phenylhydrazone. 1-Benzothiophene-3-carbaldehyde phenylhydrazone may be prepared according to the preparation procedure above for 9-ethyl-3-carbazolecarbaldehyde phenylhydrazone except that 9-ethyl-3-carbazolecarbaldehyde is replaced by 1-benzothiophene-3-carbaldehyde which is available from Aldrich, Milwaukee, Wis.

Compound (7)

Compound (7) may be prepared according to the preparation procedure above for Compound (1) except that 9-ethyl-3-carbazolecarbaldehyde phenylhydrazone is replaced by 1-benzofuran-2-carbaldehyde phenylhydrazone. 1-Benzofuran-2-carbaldehyde phenylhydrazone may be prepared according to the preparation procedure above for 9-ethyl-3-carbazolecarbaldehyde phenylhydrazone except that 9-ethyl-3-carbazolecarbaldehyde is replaced by 1-benzofuran-2-carbaldehyde which is available from Aldrich, Milwaukee, Wis.

Example 2

Charge Mobility Measurements

This example describes the measurement of charge mobility and ionization potential for charge transport materials, specifically Compounds (1), (2), and (3).

Sample 1

A mixture of 0.1 g of Compound (1) and 0.1 g of polycarbonate Z was dissolved in 2 ml of tetrahydrofuran (THF). The solution was coated on a polyester film with a conductive aluminum layer by a trough coating (or "dip roller") method (where the substrate was affixed to a roller that rotated through a trough containing the coating solution). After the coating was dried for 1 hour at 80° C., a clear 10 μm thick layer was formed. The hole mobility of the sample was measured and the results are presented in Table 1.

Sample 2

A mixture of 0.1 g of Compound (3) and 0.1 g of polycarbonate Z was dissolved in 2 ml of tetrahydrofuran (THF). The solution was coated on a polyester film with a conductive aluminum layer by a trough coating (or "dip roller") method (where the substrate was affixed to a roller that rotated through a trough containing the coating solution). After the coating was dried for 1 hour at 80° C., a clear 10 μm thick layer was formed. The hole mobility of the sample was measured and the results are presented in Table 1.

Sample 3

A mixture of 0.1 g of Compound (2) and 0.1 g of polycarbonate Z was dissolved in 2 ml of tetrahydrofuran (THF). The solution was coated on a polyester film with a conductive aluminum layer by a trough coating (or "dip roller") method (where the substrate was affixed to a roller that rotated through a trough containing the coating solution). After the coating was dried for 1 hour at 80° C., a clear 10 μm thick layer was formed. The hole mobility of the sample was measured and the results are presented in Table 1.

Sample 4

A mixture of 0.1 g of Compound (4) and 0.1 g of polycarbonate Z was dissolved in 2 ml of tetrahydrofuran (THF). The solution was coated on a polyester film with a conductive aluminum layer by a trough coating (or "dip roller") method (where the substrate was affixed to a roller that rotated through a trough containing the coating solution). After the coating was dried for 1 hour at 80° C., a clear 10 μm thick layer was formed. The hole mobility of the sample was measured and the results are presented in Table 1.

Sample 5

A mixture of 0.1 g of Compound (5) and 0.1 g of polycarbonate Z was dissolved in 2 ml of tetrahydrofuran (THF). The solution was coated on a polyester film with a conductive aluminum layer by a trough coating (or "dip roller") method (where the substrate was affixed to a roller that rotated through a trough containing the coating solution). After the coating was dried for 1 hour at 80° C., a clear 10 μm thick layer was formed. The hole mobility of the sample was measured and the results are presented in Table 1.

Mobility Measurements

Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747-752, incorporated herein by reference. The hole mobility measurement was repeated with appropriate changes to the charging regime to charge the sample to different U values, which corresponded to different electric field strength inside the layer E. This dependence on electric field strength was approximated by the formula $$\mu = \mu_0 e^{\alpha \sqrt{E}}.$$

Here E is electric field strength, $\mu_0$ is the zero field mobility and α is Pool-Frenkel parameter. Table 1 lists the mobility characterizing parameters $\mu_0$ and α values and the mobility value at the $6.4 \times 10^5$ V/cm field strength as determined by these measurements for the samples.

TABLE 1

| Example | $\mu_0$ (cm$^2$/V · s) | μ (cm$^2$/V · s) at 6.4 · 10$^5$ V/cm | α (cm/V)$^{0.5}$ | Ionization Potential (eV) |
|---|---|---|---|---|
| Sample 1 | $9.0 \times 10^{-9}$ | $2.4 \times 10^{-6}$ | 0.0070 | / |
| Compound (1) | / | / | / | 5.50 |
| Sample 2 | $\sim 7.0 \times 10^{-10}$ | $2.8 \times 10^{-7}$ | ~0.0076 | / |
| Compound (3) | / | / | / | 5.53 |
| Sample 3 | $3.5.0 \times 10^{-8}$ | $7.3 \times 10^{-6}$ | 0.0067 | / |
| Compound (2) | / | / | / | 5.37 |
| Sample 4 | $6 \cdot 10^{-10}$ | $4 \cdot 10^{-7}$ | 0.0082 | / |
| Compound 4 | / | / | / | 5.50 |
| Sample 5 | $3.4 \cdot 10^{-8}$ | $2.9 \cdot 10^{-6}$ | 0.0055 | / |
| Compound 5 | / | / | / | 5.43 |

Example 3

Ionization Potential Measurements

This example describes the measurement of the ionization potential for the charge transport materials described in Example 1.

To perform the ionization potential measurements, a thin layer of a charge transport material about 0.5 μm thickness was coated from a solution of 2 mg of the charge transport material in 0.2 ml of tetrahydrofuran on a 20 cm$^2$ substrate surface. The substrate was an aluminized polyester film coated with a 0.4 μm thick methylcellulose sub-layer.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127-131, incorporated herein by reference. In particular, each sample was illuminated with monochromatic light from the quartz monochromator with a deuterium lamp source. The power of the incident light beam was 2-5·10-8 W. A negative voltage of −300 V was supplied to the sample substrate. A counter-electrode with the 4.5×15 mm$^2$ slit for illumination was placed at 8 mm distance from the sample surface. The counter-electrode was connected to the input of a BK2-16 type electrometer, working in the open input regime, for the photocurrent measurement. A $10^{-15}$-$10^{-12}$ amp photocurrent was flowing in the circuit under illumination. The photocurrent, I, was strongly dependent on the incident light photon energy hv. The $I^{0.5}=f(hv)$ dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography*, 28, Nr. 4, p. 364 (1989) by E. Miyamoto, Y. Yamaguchi, and M. Yokoyama; and "Photoemission in Solids," Topics in Applied Physics, 26, 1-103 (1978) by M. Cordona and L. Ley, both of which are incorporated herein by reference). The linear part of this dependence was extrapolated to the hv axis, and the Ip value was determined as the photon energy at the interception point. The ionization potential measurement has an error of ±0.03 eV. The ionization potential values are given in Table 1 above.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

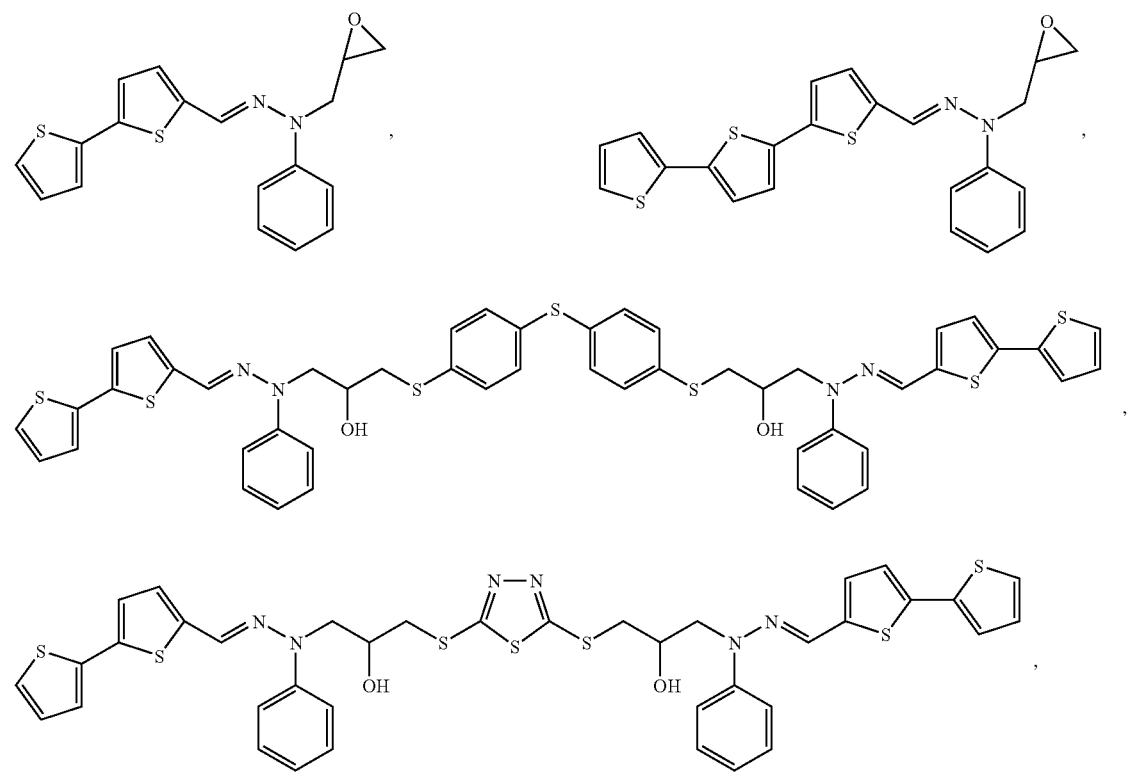

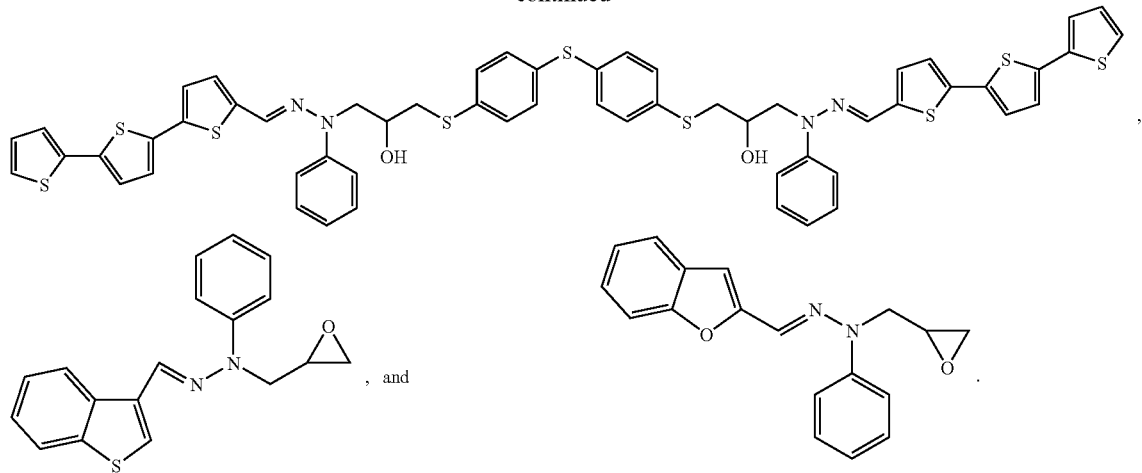

What is claimed is:

1. An organophotoreceptor comprising an electrically conductive substrate and a photoconductive element on the electrically conductive substrate, the photoconductive element comprising:

(a) a charge transport material having the formula:

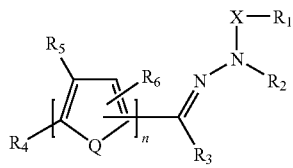

where n is an integer between 1 and 10, inclusive;

R1 comprises a functional group selected from the group consisting of a reactive ring group, an ethylenically unsaturated group, a hydrazone group, and an azine group;

$R_2$, $R_3$, and $R_4$ comprise, each independently, H, an alkyl group, an alkenyl group, an alkynyl group, an aromatic group, a heterocyclic group, or a part of a ring group;

$R_5$ and R6 comprise, each independently, H, an alkyl group, an alkenyl group, an alkynyl group, an aromatic group, a heterocyclic group, or a part of a ring group wherein the ring group is not part of a heterocyclic group;

wherein $R_4$ and $R_5$ together form a benzo ring and n is 1;

X is a bond or a linking group; and

Q is O, S, or NR where R is H, an alkyl group, an acyl group, an alkenyl group, an alkynyl group, a heterocyclic group, or an aromatic group; and (b) a charge generating compound.

2. An organophotoreceptor according to claim 1 wherein X is a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a P(=O)$R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, an alkynyl group, a heterocyclic group, an aromatic group, a part of a ring group, or an alkyl group where one or more of the hydrogens of the alkyl group is optionally replaced by an aromatic group, a hydroxyl group, a thiol group, a carboxyl group, an amino group, or a halogen.

3. An organophotoreceptor according to claim 1 wherein $R_1$ is selected from the group consisting of an epoxy group, a thiiranyl group, an aziridinyl group, an oxetanyl group, a vinyl ether group, an alkenyl group, an acryloyl group, a methacryloyl group, an acrylamido group, and a methacrylamido group.

4. An organophotoreceptor according to claim 1 wherein Q is S and n is an integer between 2 and 5, inclusive.

5. An organophotoreceptor according to claim 2 wherein $R_1$ comprises a heterocycle hydrazone group having the formula:

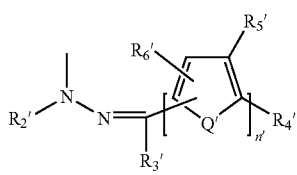

where n' is an integer between 1 and 10, inclusive;

$R_2'$, $R_3'$, $R_4'$, $R_5'$, and $R_6'$ comprise, each independently, H, an alkyl group, an alkenyl group, an alkynyl group, an aromatic group, a heterocyclic group, or a part of a ring group; and Q' is O, S, or $NR_7$ where $R_7$ is H, an alkyl group, an acyl group, an alkenyl group, an alkynyl group, a heterocyclic group, or an aromatic group.

6. An organophotoreceptor according to claim 5 wherein X has the formula:

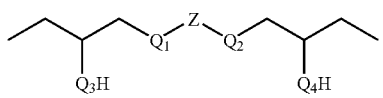

where $Q_1$, $Q_2$, $Q_3$, and $Q_4$ are, each independently, O, S, or $NR_8$; and Z comprises a bond, an alkylene group, an aromatic group, a heterocyclic group, or a combination thereof, wherein $R_8$ is H, an alkyl group, an acyl group, an alkenyl group, an alkynyl group, a heterocyclic group, or an aromatic group.

7. An organophotoreceptor according to claim 6 wherein Q1 and $Q_2$ are each S, $Q_3$ and $Q_4$ are each O, and Z is a formula selected from the group consisting of:

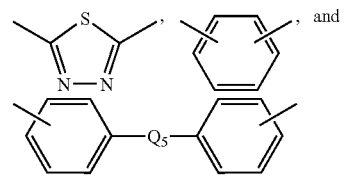

where $Q_5$ is a bond, O, S, or $NR_9$, and $R_9$ is H, an alkyl group, an acyl group, an alkenyl group, an alkynyl group, a heterocyclic group, or an aromatic group, and Z may have one or more substituents.

8. An organophotoreceptor according to claim 7 wherein Z further comprises at least one substituent selected from the group consisting of a hydroxyl group, a thiol group, a carboxyl group, an amino group, a halogen, an alkyl group, an acyl group, an alkoxy group, an alkylsulfanyl group, an alkenyl group, an alkynyl group, an ester group, an amido group, a nitro group, a cyano group, a sulfonate group, a phosphate, phosphonate, a heterocyclic group, an aromatic group, a hydrazone group, an enamine group, an azine group, an epoxy group, a thiiranyl group, and an aziridinyl group.

9. An organophotoreceptor according to claim 1 wherein the photoconductive element further comprises a second charge transport material.

10. An organophotoreceptor according to claim 9 wherein the second charge transport material comprises an electron transport compound.

11. An organophotoreceptor according to claim 1 wherein the photoconductive element further comprises a binder.

12. An electrophotographic imaging apparatus comprising:

(a) a light imaging component; and (b) an organophotoreceptor oriented to receive light from the light imaging component, the organophotoreceptor comprising an electrically conductive substrate and a photoconductive element on the electrically conductive substrate, the photoconductive element comprising:

(i) a charge transport material having the formula:

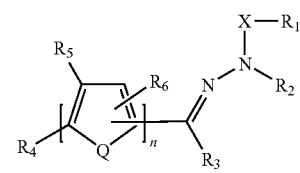

where n is an integer between 1 and 10, inclusive;

$R_1$ comprises; a heterocycle hydrazone group having the formula:

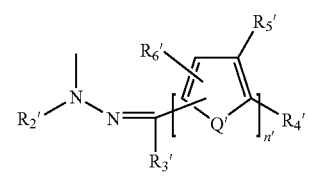

where n' is an integer between 1 and 10, inclusive;

$R_2'$—, $R_3'$, $R_4'$—, $R_5'$, and $R_6'$ comprise, each independently, H, an alkvl group, an alkenyl group, an alkynyl group, an aromatic group, a heterocyclic group, or a part of a ring group; and $Q'$ is O, S, or $NR_7$ where $R_7$ is H, an alkyl group, an acyl group, an alkenyl group, an alkynyl group, a heterocyclic group, or an aromatic group;

$R_2$, $R_3$, and $R_4$ comprise, each independently, H, an alkyl group, an alkenyl group, an alkynyl group, an aromatic group, a heterocyclic group, or a part of a ring group;

$R_5$ and $R_6$ comprise, each independently, H, an alkyl group, an alkenyl group, an alkynyl group, an aromatic group, or a part of a ring group wherein the ring group is not part of a heterocyclic group;

X a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group an amino group, a halogen, an acyl group, an alkoxy group, an alkylsulfanyl group, an alkenyl group, an alkynyl group, a heterocyclic group, an aromatic group, a part of a ring group, or an alkyl group where one or more of the hydro gens of the alkyl group is optionally replaced by an aromatic group, a hydroxyl group, a thiol group. a carboxyl group, an amino group, or a halogen; and Q is O, S, or NR where R is H, an alkyl group, an acyl group, an alkenyl group, an alkynyl group, a heterocyclic group, or an aromatic group; and (ii) a charge generating compound.

13. An electrophotographic imaging apparatus according to claim 12 further comprising a toner dispenser.

14. An electrophotographic imaging process comprising;
(a) applying an electrical charge to a surface of an organophotoreceptor comprising an electrically conductive substrate and a photoconductive element on the electrically conductive substrate, the photoconductive element comprising
(i) a charge transport material having the formula:

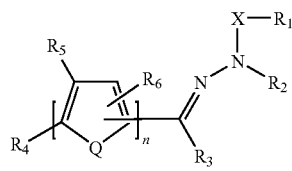

where n is an integer between 1 and 10, inclusive;
$R_1$ comprises a functional group selected from the group consisting of a reactive ring group, an ethylenically unsaturated group, a hydrazone group, and an azine group;
$R_2$ $R_3$, and $R_4$, comprise, each independently, H, an alkyl group, an alkenyl group, an alkynyl group, an aromatic group, a heterocyclic group, or a part of a ring group;
$R_5$ and $R_6$ comprise, each independently, H, an alkyl group, an alkenyl group, an alkynyl group, an aromatic group, a heterocyclic group, or a part of a ring group wherein the ring group is not part of a heterocyclic group;
wherein $R_4$ and $R_5$ together form a benzo ma and n is 1;
X is a bond or a linking group; and Q is O, S, or NR where R is H, an alkyl group, an acyl group, an alkenyl group, an alkynyl group, a heterocyclic group, or an aromatic group; and (ii) a charge generating compound;

(b) imagewise exposing the surface of the organophotoreceptor to radiation to dissipate charge in selected areas and thereby form a pattern of charged and uncharged areas on the surface;

(c) contacting the surface with a toner to create a toned image; and (d) transferring the toned image to a substrate.

15. An electrophotographic imaging process according to claim 14 wherein X is a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an ailcoxy group, an alkylsulfanyl group, an alkenyl group, an alkynyl group, a heterocyclic group, an aromatic group, a part of a ring group, or an alkyl group where one or more of the hydrogens of the alkyl group is optionally replaced by an aromatic group, a hydroxyl group, a thiol group, a carboxyl group, an amino group, or a halogen.

16. An electrophotographic imaging process according to claim 14 wherein $R_1$ is selected from the group consisting of an epoxy group, a thiiranyl group, an aziridinyl group, an oxetanyl group, a vinyl ether group, an alkenyl group, an acryloyl group, a methacryloyl group, an acrylamido group, and a methacrylamido group.

17. An electrophotographic imaging process according to claim 14 wherein the toner comprises colorant particles.

18. A charge transport material, having the formula:

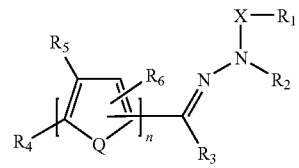

where n is an integer between 1 and 10, inclusive;
R1 comprises a functional group selected from the group consisting of a reactive ring group, an ethylenically unsaturated group, a hydrazone group, and an azine group;
$R_2$, R3, and R4, comprise, each independently, H, an alkyl group, an alkenyl group, an alkynyl group, an aromatic group, a heterocyclic group, or a part of a ring group;
$R_5$ and R6 comprise, each independently, H, an alkyl group, an alkenyl group, an alkynyl group, an aromatic group, a heterocyclic group, or a part of a ring group wherein the ring group is not part of a heterocyclic group;
wherein $R_4$ and $R_5$ together form a benzo ring and n is 1;
X is a bond or a linking group; and
Q is O, S, or NR where R is H, an alkyl group, an acyl group, an alkenyl group, an alkynyl group, a heterocyclic group, or an aromatic group.

19. A charge transport material according to claim 18 wherein X is a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_d$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, an alkynyl group, a heterocyclic group, an aromatic group, a part of a ring group, or an alkyl group where one or more of the hydrogens of the alkyl group is optionally replaced by an aromatic group, a hydroxyl group, a thiol group, a carboxyl. group, an amino group, or a halogen.

20. A charge transport material according to claim 18 wherein $R_1$ is selected from the group consisting of an epoxy group, a thiiranyl group, an aziridinyl group, an oxetanyl group, a vinyl ether group, an alkenyl group, an acryloyl group, a methacryloyl group, an acrylamido group, and a methacrylamido group.

21. A charge transport material according to claim 18 wherein Q is S and n is an integer between 2 and 5, inclusive.

22. A charge transport material according to claim 19 wherein $R_1$ comprises a heterocycle hydrazone group having the formula:

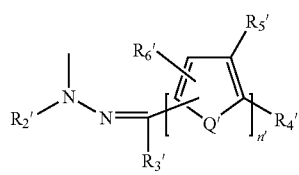

where n' is an integer between 1 and 10, inclusive; $R_2'$, $R_3'$, $R_4'$, $R_5'$, and $R_6'$ comprise, each independently, H, an alkyl group, an alkenyl group, an alkynyl group, an aromatic group, a heterocyclic group, or a part of a ring group; and Q' is O, S, or $NR_7$ where $R_7$ is H, an alkyl group, an acyl group, an alkenyl group, an alkynyl group, a heterocyclic group, or an aromatic group.

23. A charge transport material according to claim 22 wherein X has the formula:

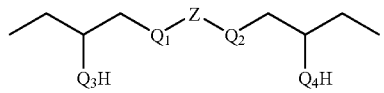

where $Q_1$, $Q_2$, $Q_3$, and $Q_4$ are, each independently, O, S, or $NR_8$; Z comprises a bond, an alkylene group, an aromatic group, a heterocyclic group, or a combination thereof; and $R_8$ is H, an alkyl group, an acyl group, an alkenyl group, an alkynyl group, a heterocyclic group, or an aromatic group.

24. A charge transport material according to claim 23 wherein $Q_1$ and $Q_2$ are each S, $Q_3$ and $Q_4$ are each O, and Z is a formula selected from the group consisting of:

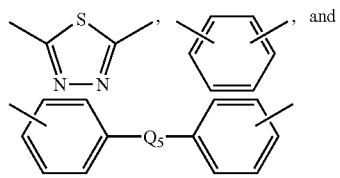

where $Q_5$ is a bond, O, S, or $NR_9$, and $R_9$ is H, an alkyl group, an acyl group, an alkenyl group, an alkynyl group, a heterocyclic group, or an aromatic group, and Z may have one or more substituents.

25. A charge transport material according to claim 18 wherein the charge transport material is selected from the group consisting of the following structures:

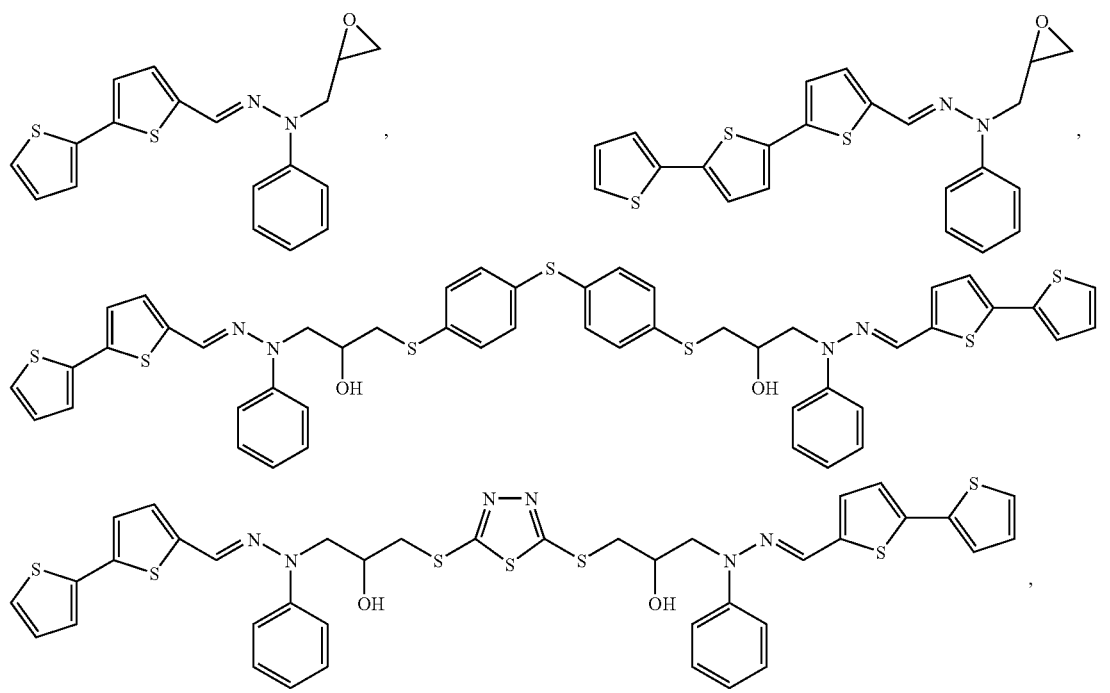

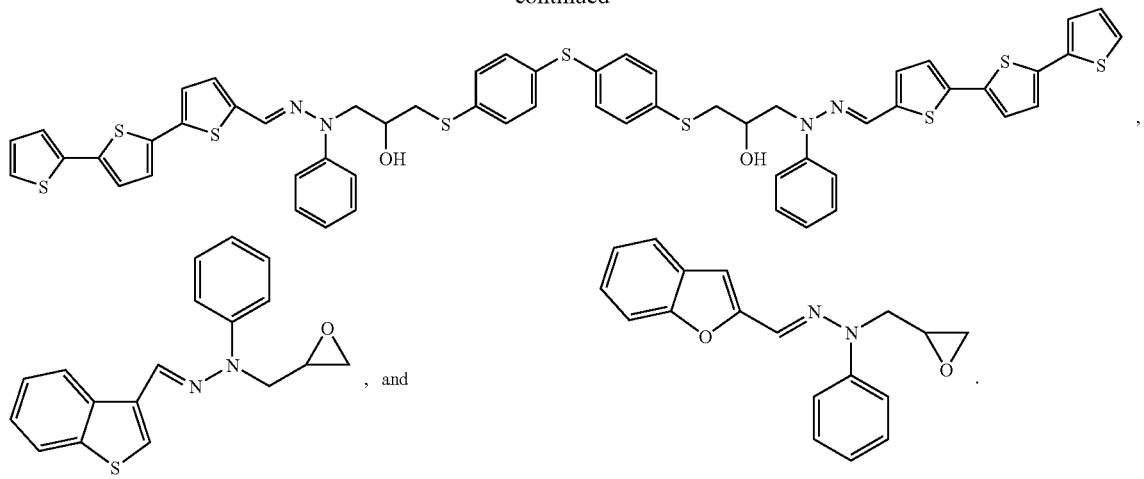

26. An organophotoreceptor according to claim 24 wherein the charge transport material further comprises at least one substituent selected from the group consisting of a hydroxyl group, a thiol group, a carboxyl group, an amino group, a halogen, an alkyl group, an acyl group, an alkoxy group, an alkylsulfanyl group, an alkenyl group, an alkynyl group, an ester group, an anildo group, a nitro group, a cyano group, a sulfonate group, a phosphate, phosphonate, a heterocyclic group, an aromatic group, a hydrazone group, an enamine group, an azine group, an epoxy group, a thiiranyl group, and an aziridinyl group.

27. A charge transport material having the formula:

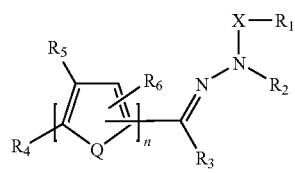

selected from the group consisting of the following structures: